(12) United States Patent
Rader et al.

(10) Patent No.: US 6,944,474 B2
(45) Date of Patent: Sep. 13, 2005

(54) SOUND ENHANCEMENT FOR MOBILE PHONES AND OTHER PRODUCTS PRODUCING PERSONALIZED AUDIO FOR USERS

(75) Inventors: R. Scott Rader, Menlo Park, CA (US); Christoph Menzel, Madison, CT (US); Brent W. Edwards, San Francisco, CA (US); Sunil Puria, Mountain View, CA (US); Benny B. Johansen, Sunnyvale, CA (US)

(73) Assignee: Sound ID, Palo Alto, CA (US)

( * ) Notice: Subject to any disclaimer, the term of this patent is extended or adjusted under 35 U.S.C. 154(b) by 497 days.

(21) Appl. No.: 09/957,344

(22) Filed: Sep. 20, 2001

(65) Prior Publication Data

US 2003/0064746 A1 Apr. 3, 2003

(51) Int. Cl.[7] .............................................. H04M 1/00
(52) U.S. Cl. ............................. 455/550.1; 455/432.3; 455/72; 704/271
(58) Field of Search ............................... 455/432, 268, 455/72, 69, 550.1, 517; 379/390.01, 388.03, 388.05, 390.03; 381/106, 321, 221, 60, 315; 704/225, 271

(56) References Cited

U.S. PATENT DOCUMENTS 4,731,850 A    3/1988  Levitt et al.

6,463,128 B1 * 10/2002 Elwin .......................... 379/52

FOREIGN PATENT DOCUMENTS

JP     2000-209698 A1    7/2000
JP     2000-209698    *  7/2000   ........... H04R/25/00

* cited by examiner

Primary Examiner—Melur Ramakrishnaiah
(74) Attorney, Agent, or Firm—Haynes Beffel & Wolfeld LLP

(57) ABSTRACT

A mobile phone or other personal communication device includes resources applying measures of an individual's hearing profile, personal choice profile, and induced hearing loss profile, separately or in combination, to build the basis of sound enhancement. A personal communication device thus comprises a transmitter/receiver coupled to a communication medium for transmitted receiving audio signals, control circuitry that controls transmission, reception and processing of call and audio signals, a speaker, and a microphone. The control circuitry includes logic applying one or more of a hearing profile of the user, a user preference related hearing, and environmental noise factors in processing the audio signals. The control circuitry may includes instruction memory and an instruction execution processor such as a digital signal processor.

41 Claims, 9 Drawing Sheets

FIG. 11
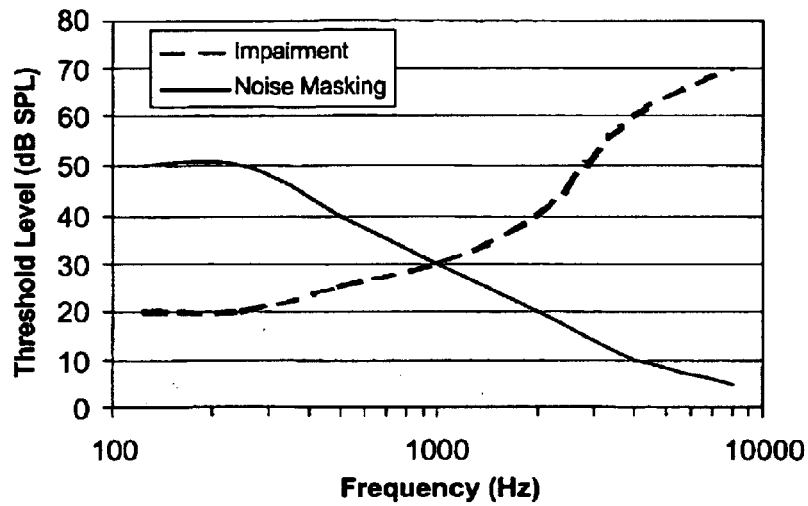
FIG. 12a
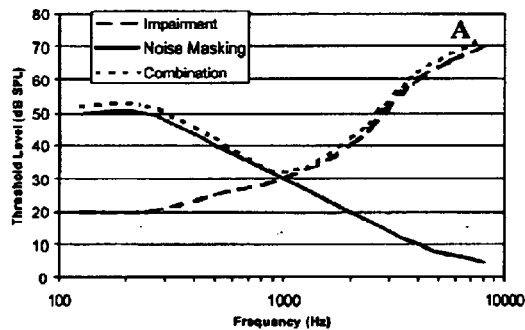
FIG. 12b
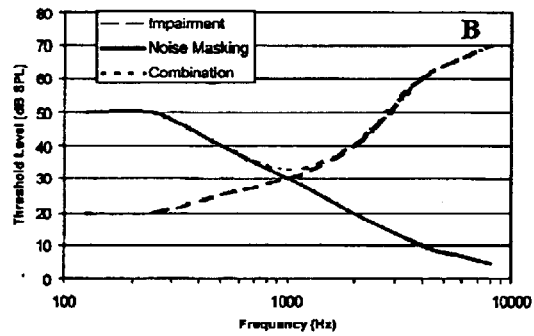
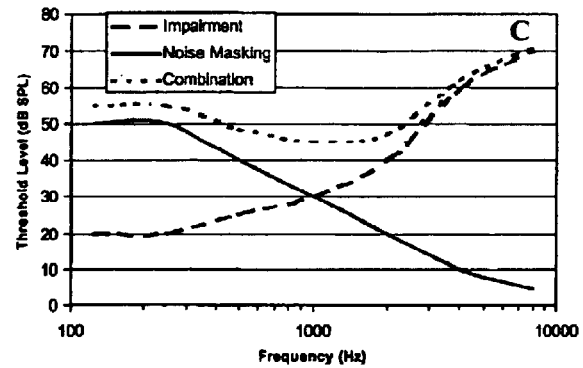
FIG. 12c

SOUND ENHANCEMENT FOR MOBILE PHONES AND OTHER PRODUCTS PRODUCING PERSONALIZED AUDIO FOR USERS

BACKGROUND OF THE INVENTION

1. Field of the Invention

The present invention relates the field of sound enhancement for mobile phones and other products which produce audio for users, and more particularly to techniques for enhancing sound based upon an individual's hearing profile, based upon environmental factors like noise-induced hearing impairment, and based on personal choice.

2. Description of Related Art

Assessing an individual's hearing profile is important in a variety of contexts. For example, individuals with hearing profiles that are outside of a normal range, must have their profile recorded for the purposes of prescribing hearing aids which fit the individual profile. Typically hearing profile assessments are made by professional audiologists using calibrated and specialized equipment. Therefore, hearing profile assessments have been relatively difficult to obtain and expensive.

A variety of uses for hearing profiles, other than for the purposes of prescribing hearing aids and assistive listening devices, is being developed. For example, hearing profiles of individuals can be utilized for producing customized audio products, such as pre-recorded music that has been modified according to the hearing profile of the listener. One medium for delivering customized audio products is the Internet. See, commonly owned and copending U.S. patent application Ser. No.: 09/464,036, filed 15, Dec. 1999, by Pluvinage, et al., entitled "System and Method for Producing and Storing Hearing Profiles and Customized Audio Data Based on Such Hearing Profiles."

The mobile phone is a unique class of personal audio device, which presents difficulties to persons with hearing profiles that do not fall within the normal ranges. The most common approach to enabling use of mobile phones for hearing impaired persons involves the use of hearing aids. However, digital mobile phones can cause electromagnetic and acoustic interference with digital hearing aids, forcing removal of aids during mobile phone usage, leaving the user with no compensatory signal processing. In one innovative example, mobile phones can be coupled to inductive neck-worn loops as phone accessories, which deliver signals to electromagnetic receivers called "Telecoils" within hearing aids. However the inconvenience and small market penetration of Telecoils in hearing aids makes them a limited solution. Simply increasing amplification in cell phones is another approach with obvious drawbacks.

Previous people have suggested systems that compensate for apparent hearing loss due to background noise masking. Such prior systems are dependent on the use of microphone input signals to determine the amount of background noise. Some of these systems also teach the use of compression for such compensation. Background information including the use of compression in phones is described in Goldberg (U.S. Pat. No. 4,829,565) and Allen & Youtkas (U.S. Pat. No. 5,553,134), although primarily for noise compensation; other patents include: U.S. Pat. Nos. 5,802,164, 5,539,806, 6,061,431, 5,737,719, 5,388,185, 5,896,449 for telephone signal enhancement; U.S. Pat. Nos. 4,964,304, 6,071,236, 3,974,335, and U.S. Pat. No. 5,737,389 for hearing testing over a phone or telecommunications network.

Mobile phones are inherently personal communication devices. Innovations in microelectronics have allowed mobile phones to become extremely portable and wearable, affording access to telecommunications services wherever the service infrastructure is available. Future generation mobile phones may also incorporate entertainment features such as streaming audio and video, playback of stored audio or video, radio reception and presentation, and many other features that deliver audio to the user. It is desirable to enhance the reception of mobile phone system audio by the user, accommodating personal hearing needs, personal choice, or optimization to the noise environment surrounding the user.

SUMMARY OF THE INVENTION

The invention disclosed herein is designed to enhance the reception of audio by the listener using a personal communication device, based upon measuring a person's hearing impairment, environmental factors which are modeled as induced hearing loss, and personal choice, and then utilizing signal processing to accommodate for lost functionality of the cochlea suggested by the hearing profile, and to enhance the sound based upon environmental factors, like background noise, and personal choice.

According to the present invention, a mobile phone or other personal communication device includes resources applying measures of an individual's hearing profile, personal choice profile, and induced hearing loss profile, separately or in combination, to build the basis of sound enhancement.

A personal communication device according to the present invention comprises a transmitter/receiver coupled to a communication medium for transmitting and receiving audio signals; control circuitry that controls transmission, reception and processing of call and audio signals; a transducer such as an internal speaker, an external speaker, and a speaker in an attached headset; and an internal microphone, an external microphone, and a microphone in an attached headset. The control circuitry includes logic applying one or more of a hearing profile of the user, a user preference related hearing, and environmental noise factors in processing the audio signals. In various embodiments of the invention, the control circuitry includes instruction memory and an instruction execution processor such as a digital signal processor.

In another embodiment, a personal communication device according to the present invention includes an input device adapted to indicate a volume level for the speaker, and wherein said control circuitry is responsive to volume level to vary multi-band compression parameters applied the audio signals.

In one embodiment, a personal communication device includes control circuitry which applies a composite profile in processing the audio signals, where the composite profile comprises a set of parameters based upon more than one of the hearing profile of the user, the user preference related hearing, and environmental noise factors. In various embodiments, the control circuitry applies more than one of the hearing profile of the user, the user preference related hearing, and environmental noise factors independently in processing the audio signals. Such processing may be done in series by the control circuitry, or in parallel.

In various embodiments, background noise levels are detected using the microphone, an extra sensor which is coupled to the device for sensing environmental noise, and by indirect measures such as the position of a volume control knob, or an indication of a location of use of the device.

In yet another embodiment, the device includes resources for obtaining a hearing profile for a user from a remote source, such as a server coupled to the communication medium. Alternatively, the device may include resources to prompt a user to provide information specifying the hearing profile of the user. In addition, the device may include resources for prompting the user to enter user preference information. In various embodiments, this device includes resources to prompt a user to provide information for use in defining a hearing profile, such as by prompting the user through a hearing test, in which audio stimuli used in the test are produced using transducers, such as the speaker on the device, a speaker attached to the device, or a speaker in a headset coupled to the device.

According to one embodiment of the invention, the personal communication device comprises a mobile phone including an antenna. In this embodiment, the transmitter/receiver comprises a radio coupled to the antenna, and the communication medium is wireless.

According to yet another embodiment of the invention, a telephone communication system is provided which comprises a service provider and a mobile phone.

Other aspects and advantages of the present invention can be seen upon review of the figures, the detailed description and claims which follow.

BRIEF DESCRIPTION OF THE DRAWING

FIG. 11 is a graph showing hearing impairment and noise thresholds used in support of an explanation of processing according to the present invention.

FIGS. 12a–12c are graphs showing various techniques for combining hearing threshold parameters in support of an explanation of processing according to the present invention.

DETAILED DESCRIPTION

Figure 1:
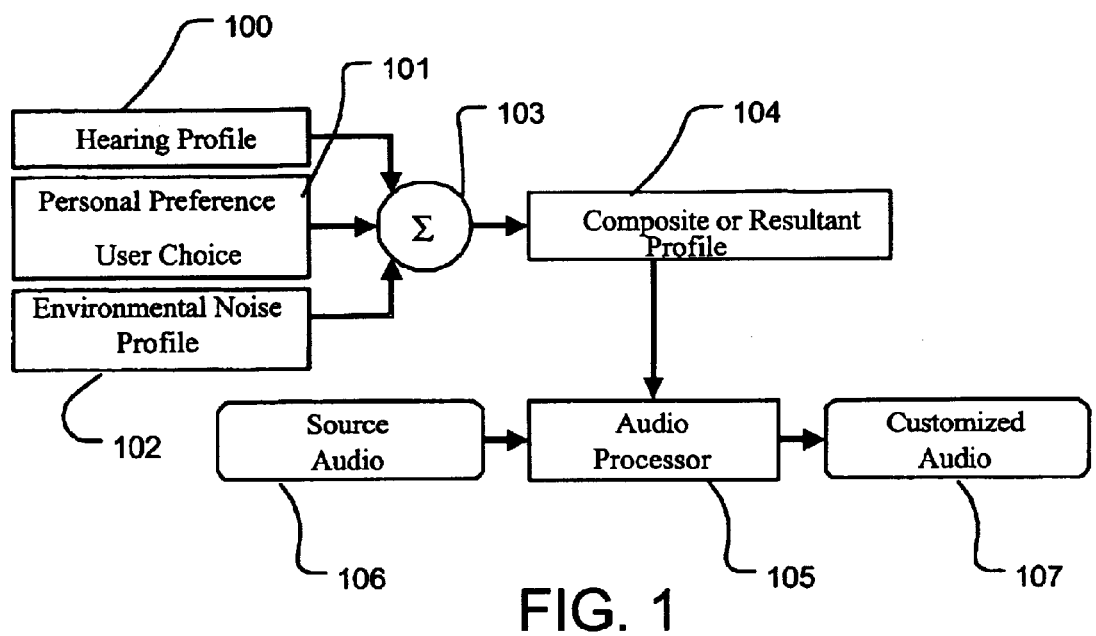
FIG. 1 is a conceptual block diagram showing the sound processing in a personal communication device according to the present invention.

A detailed description of embodiments of the present invention is provided with respect to the Figures, in which FIG. 1 illustrates how a hearing profile 100, a listener's personal choice profile 101, and/or a profile 102 of the environmental noise can be combined in a variety of ways represented by the summing node 103 into a composite or resultant profile 104 to base customization of audio for the listener. All three sub-profiles are not necessarily active at all times. As shown in FIG. 1, a audio processor 105 in an personal communication device receives the composite or resultant profile 104, and applies the profile 104 to a source audio stream 106, to provide customized audio 107, which enhances the user's reception of the audio product. The summing node 103 is used heuristically in the diagram. In various embodiments, each component 100, 101, 102 of the composite profile 104 can be used independently, in series, or in parallel in any combination. In one preferred embodiment, the personal communication device is a mobile phone.

Next generation mobile phones are incorporating features that intersect with the functionality of a small computer, music player, and organizer, and include processing resources for customizing the audio as shown in FIG. 1.

The term "personal communication device," of which the mobile phone is a preferred example, is used throughout this disclosure to indicate a system that has the capability to send and receive a wide variety of audio signals between a remote system and a network infrastructure. The personal communication device could be a very simple system designed to only send and receive voice information, or a complex system that has computational capabilities integrated with or connected to a phone sub-system. The personal communication device could also incorporate phone system attributes combined with audio playback means, where the audio is digitally stored or streamed audio, analog audio playback or other system sound generation. Mobile phones with various combinations of features displays, audio transducers, headsets, and computational tools (e.g. calender programs, contact list programs, audio playback programs, digital image displays, etc.) in addition to phone call processing are examples of personal communication devices.

Common network protocols for sending and receiving information to and from the mobile phone include AMPS (analog signal), TDMA (time division multiple access) including GSM (general system for mobile), CDMA (code division multiple access), and GPRS (general packet radio service). There are other standards that comprise a sub- or super-set of these general classification; the standards are mentioned here to include signal means between network and mobile phone that span analog, circuit-switched, analog, digital and packet based wireless services. Mobile phones adapted to communication with these protocols are provides with signal processing capability that is increasing in power and flexibility.

Irrespective of the mode of information transmission, the primary function of a personal communication device is audio signal transmission and reception.

Figure 2:
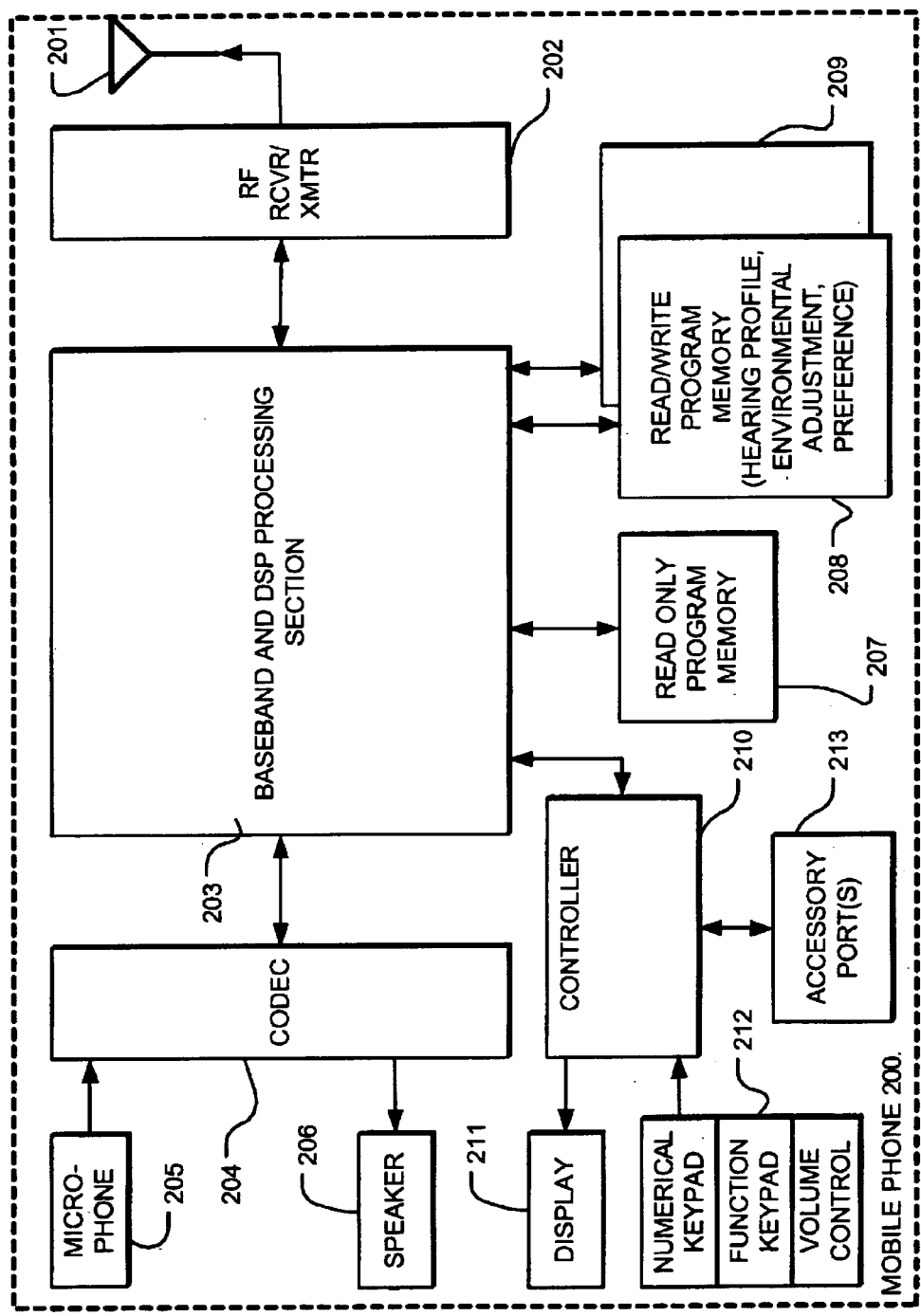
FIG. 2 is a simplified block diagram of a mobile phone, representative of personal communication devices according to the present invention.

FIG. 2 is a simplified diagram of a mobile phone 200, representative of personal communication devices according to the present invention. The mobile phone 200 includes an antenna 201 and a radio frequency RF receiver/transmitter 202, by which the phone 200 is coupled to a wireless communication medium, according to one or more of a variety of protocols. The receiver/transmitter 202 is coupled to baseband and digital signal processor DSP processing section 203, in which the audio signals are processed and call signals are managed. A codec 204, including analog to digital and digital to analog converters, is coupled to the processing section 203. A microphone 205 and a speaker 206 are coupled to the codec 204.

Read only program memory 207 stores instructions, parameters and other data for execution by the processing section 203. In addition, a read/write memory 208 stores instructions, parameters and other data for use by the processing section 203. There may be multiple types of read/write memory on the device 200, such as non volatile read/write memory 208 (flash memory or EEPROM for example) and volatile read write memory 209 (DRAM or SRAM for example), as shown in FIG. 2. Other embodiments include removable memory modules in which instructions, parameters and other data for use by the processing section 203 are stored.

An input/output controller 210 is coupled to a display 211, to user input devices 212, such as a numerical keypad, a function keypad, and a volume control switch, and to an accessory port (or ports) 213. The accessory port or ports 213 are used for other types of input/output devices, such as binaural and monaural headphones, connections to processing devices such as PDAs, or personal computers, alternative communication channels such as an infrared port or Universal Serial Bus USB port, a portable storage device port, and other things. The controller 210 is coupled to the processing section 203. User input concerning call set up and management, and concerning use of the hearing profile, user preference and environmental noise factors is received via the input devices 212 and optionally via accessories. User interaction is enhanced, and the user is prompted to interact, using the display 211 and optionally other accessories. Input may also be received via the microphone 205 supported by voice recognition programs, and user interaction and prompting may utilize the speaker 206 for various purposes.

In this embodiment of the present invention, the composite or resultant hearing profile 104 of FIG. 1 is stored in the read/write program memory 208. In addition, instructions for algorithms are stored in the memory 207–209 for use in applying the profile information during the processing of the audio signals.

At any given frequency, the threshold of audibility of a tone can be elevated by a hearing loss at that frequency and by masking of that frequency by competing noise. For normal hearing listeners, the amount of masking at any frequency can be calculated by filtering the amount of noise power out of an auditory filter centered at the frequency of interest. When someone has a hearing loss, there are two factors that can affect audibility at that frequency: the hearing loss and the masking from the noise. Accurately determining the combined result of these two effects is important in order to properly set the parameters of the signal processing algorithm that compensates for reduced audibility. Given the spectral density of a noise, the masked threshold can be calculated for someone with normal hearing by the application of normal auditory filters. The masked threshold of someone with a hearing impairment will depend on the combination of the masking level of the noise and the level of the impairment at each frequency. The threshold from the combined effect (THtot) should be predictable from the threshold due to the impairment (THi) and the masked threshold for normals (THm). In alternative systems, the threshold due to impairment THi could be replaced by, or supplemented with, a threshold parameter THc provided in response to information about a users personal choice, where the subscript "c" represents personal choice for profile.

The solid line in FIG. 11 shows a hypothetical hearing loss and the dashed line shows a hypothetical masked threshold for someone with normal hearing resulting from noise. In this example, and in general, noise dominates audibility in the low frequencies and hearing loss dominates audibility in the high frequencies.

Three possible ways of combining the hearing loss threshold and the normal masked threshold to predict the combined effect demonstrated in FIGS. 12a–12c. Simple taking the maximum of either threshold function as the combined threshold is shown in FIG. 12a. This function is represented by $$THtot = max(THi, THm)$$

and is represented by the dotted line, which has been displaced upwards by 1 dB in order to see the curve in the presence of the other two.

A second possibility is shown by the dotted line in FIG. 12b and results from summing the powers of each threshold. This is represented by $$THtot = 10 \log 10[10^{\wedge}(THi/10) + 10^{\wedge}(THm/10)].$$

With this function, the combined eff effect is primarily to take the maximum except in the region where the thresholds are equal where there is an elevating of the combined threshold.

The third and preferred implementation is to combine them in a way that takes into account the compressive properties of the auditory system. This is demonstrated with the dotted line in FIG. 12c and is represented by $$THtot = 10 \log 10[\{10^{\wedge}(p*THi/10) + 10^{\wedge}(p*THm/10) - 10^{\wedge}(p*THn/10)\}^{\wedge}(1/p)]$$

Where THn is the threshold of the normal hearing listener. This function is from Jesteadt et. al (1995). The parameter p represents the amount of compression used during the summation and in the example given has a value of 0.2. This method of calculating the combined effect is consistent with experimental data obtained with hearing impaired subjects.

As mentioned before, THc could also be used in these and similar equations for providing an effective combined profile of a user in a noisy environment.

The effect environmental noise on auditory perception is to reduce the dynamic range available for sounds above the masking level of the environmental noise and to cause abnormal loudness perception of sound heard simultaneously with the noise. Sound ID's Full Frequency Dynamic Compression (FFDC) replicates the compressive function of the healthy cochlea, compressing sound such that the audio signal is no longer distorted in the auditory system and perception is restored to normal.

Compression is functionally an automatic gain control (AGC) within the personal communication device, where the gain reduces as the signal level increases. In order to properly compensate for reduced audibility from the environmental noise, the compression processes the signal in the same way that the cochlea's AGC processes sound in a quiet environment. The input-output function of such a compressor when measured with a quasi-steady-state pure-tone will have a compressive region that has a slope less than or equal to one over a wide dynamic input range (>40 dB), with possible linear regions below and above the compressive region. The gain and compression ratio can vary with frequency and will be monotonic with the noise power in that frequency region. The slope of the compressive region can have values that restore loudness perception to normal in that frequency region, and will have slopes that range from 1 (no compression) to 1/3 (3:1 compression). Because the amount of gain added at any frequency is a function of the power of the signal in that frequency region, the compressor calculates power and applies gain using auditory filter bandwidths that replicate normal critical bands in human hearing. The AGC may be implemented using software executed by a processor in the personal communication device, or by dedicated circuits, or by a combination of these techniques.

Figure 3:
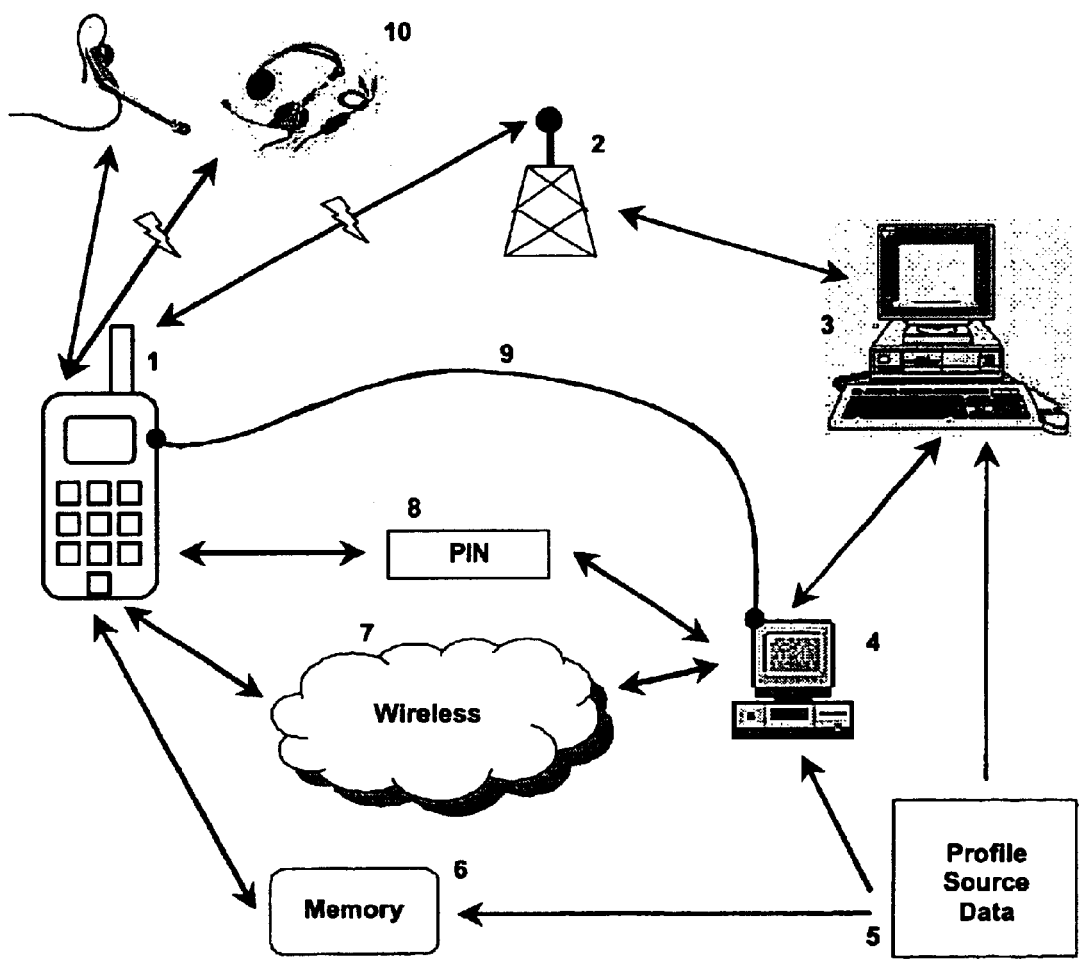
FIG. 3 illustrates a communication network, such as a telephone network, providing for hearing profile generation and transfer according various embodiments of the present invention.

FIG. 3 is a schematic representation of possible methods of acquiring a hearing profile with sub-components of an entire mobile phone system. The mobile phone 1 can be used to present acoustic stimuli, obtain user feedback, and calculate the hearing profile of an individual using only on-board memory and processing systems. Mobile phones communicate with remote systems or other phones through cellular transceivers 2. Another method for presenting acoustic stimuli would be through the use of a remote system 3 for generation of stimuli and possibly reception of user feedback. Acoustic stimuli presentation and user response could be managed at either the mobile phone 1 or at the remote system 3 in any combination.

The processing system 4 shown in FIG. 3 may be computation resources that are not on board the mobile phone, but may be in close proximity. Examples could be a base station for a handset mounted in an automobile, a telematics system that communicates to the handheld unit, or a mobile computer (or PDA) with processing resources independent of the systems of the mobile phone. The processing system of 4 could have the hearing profile of the listener pre-loaded or transmitted to it by a data source 5. Once the profile is transferred to the processing system 4, the hearing profile could be transferred to the mobile phone via a wireless local transfer 7, presentation of a PIN (personal identification number) to a user to type in or transfer of a PIN 8 into the mobile phone 1, or through a direct (such as via a wire) connection 9. Independently of a processing system 4, a hearing profile could be transferred to the mobile phone 1 by a memory storage medium 6, or through the transmission system incorporating the remote system 3, the transceiver system 2, and wireless transmission to the resources of the mobile phone 1 for incorporation of the profile into the memory or audio processor of the mobile phone 1. Protocols such as the Wireless Short Message Service SMS which is in common use with mobile phones, can be used for downloading programs and data to support the loading of a hearing profile on a phone or other personal communication device.

The processing system 4 could also be the source of profile algorithm control, acoustic stimuli generation, user feedback collection and computation of the hearing profile. The resources of 4 could be used to provide the user or the mobile phone with a PIN code, or directly transfer a profile to the mobile phone through wireless means 7 or direct connection 9. The processing resources of the mobile phone 1 and the processing system 4 could be used in multiple combinations to separate functions such as test protocol control, acoustic stimuli generation, user feedback collection, and profile calculation on either subsystem in any combination. The instructions for such functions can be provided with the phone, downloaded to the phone for execution, or stored and executed in a server which communicates with the phone during the processing, or a provided using a combination of these architectures.

Accessories 10 to the mobile phone may be used in conjunction with the mobile phone and any of the aforementioned subsystems. Accessories 10 may include, for example, monaural or binaural headphones worn by the user. The binaural headphones would allow for gathering of a hearing profile for each ear, which may become more prevalent as mobile phones become stereo audio playback devices. The accessories 10 could communicate with the mobile phone either through direct wire link or wireless link, as shown in FIG. 3.

Figure 4:
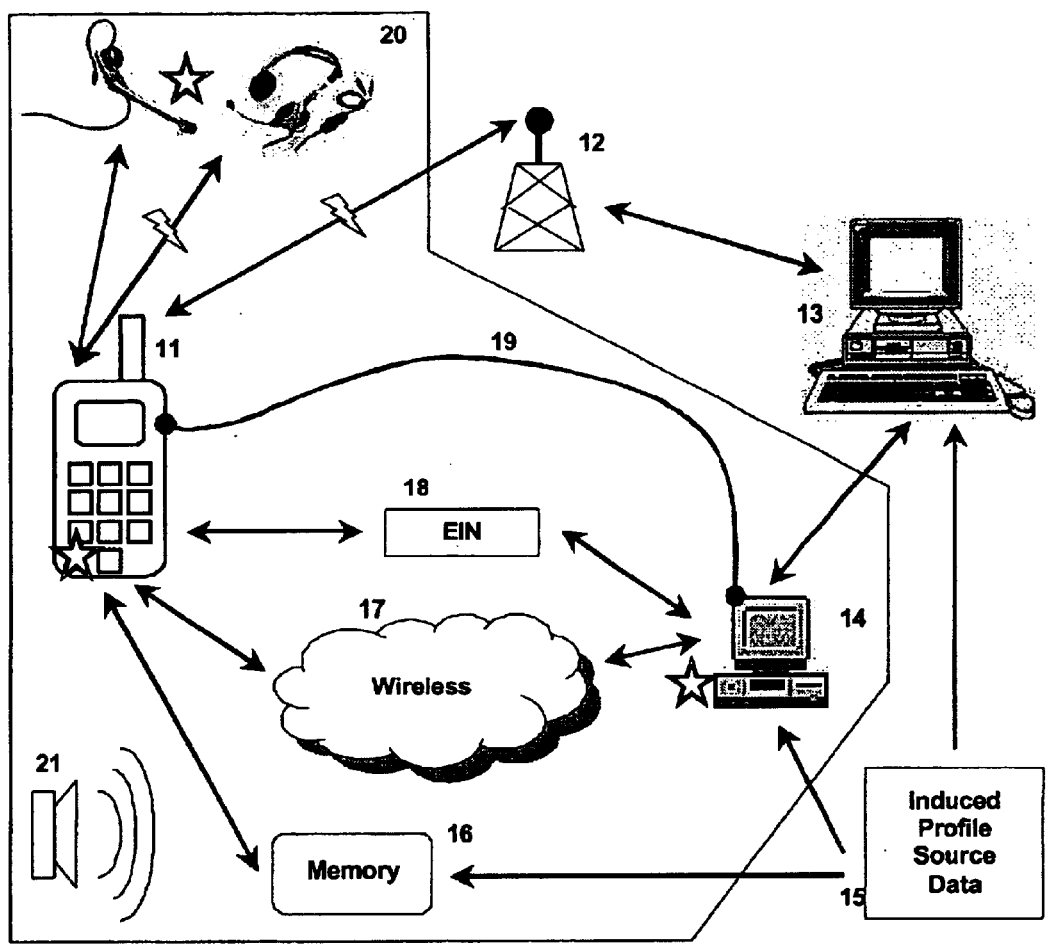
FIG. 4 illustrates a communication network, such as a telephone network, providing for induced hearing loss profile generation according to environmental factors, and transfer of such profile according various embodiments of the present invention.

Several strategies for obtaining a measure of the background noise and its concomitant induced hearing impairment are described in the schematic of FIG. 4. An environmental noise source 21 induces hearing impairment in the listener who is in proximity of the noise. The environmental noise could be sensed by a sensor (typically a microphone) on the mobile phone 11, and this information could be used by the on-board processing systems of the mobile phone with an algorithm to compensate for the induced hearing impairment.

Other strategies illustrated with respect to FIG. 4 include the possibility of sensing the noise at the phone 11, and transmitting either the noise signal or a representation of the noise signal to remote processing resources 13 through the cellular transceiver 12. The quantification of the noise, and the resultant induced profile, could be calculated at either the phone 11 or the remote processing resource 13. In a similar means, a more localized processing system 14 may be used in conjunction with the mobile phone 11 to build the induced hearing profile. The environmental sound could be sensed either at the mobile phone 11 or the processing system 14, and the resultant profile could be sent either direction for compensation processing via a wireless link 17, an "Environmental Identification Number" (EIN) shown in 18, or a direct wire link of 19.

For some environments, it may be possible to create a common induced profile 15 that could be pre-determined based on knowledge of the environment in question. This could be send to the local processing system 14 and transmitted to the phone through a wireless network 17, an EIN 18 or a direct link 19, or it may be send via the remote processing resources 13 via the cellular transceiver 12. Additionally, a predetermined induced profile 15 may be transferred to a mobile phone 11 through an external memory system 16.

Accessories 20 to the mobile phone 11 may be used to sense noise, calculate an induced hearing impairment, or even provide computational resources to customize audio. Accessories 20 such as headsets may be used to sense the local noise environment at the user's ear, and send that information to the mobile phone 11 either via a wire link or a wireless link, as shown on the diagram.

Figure 5:
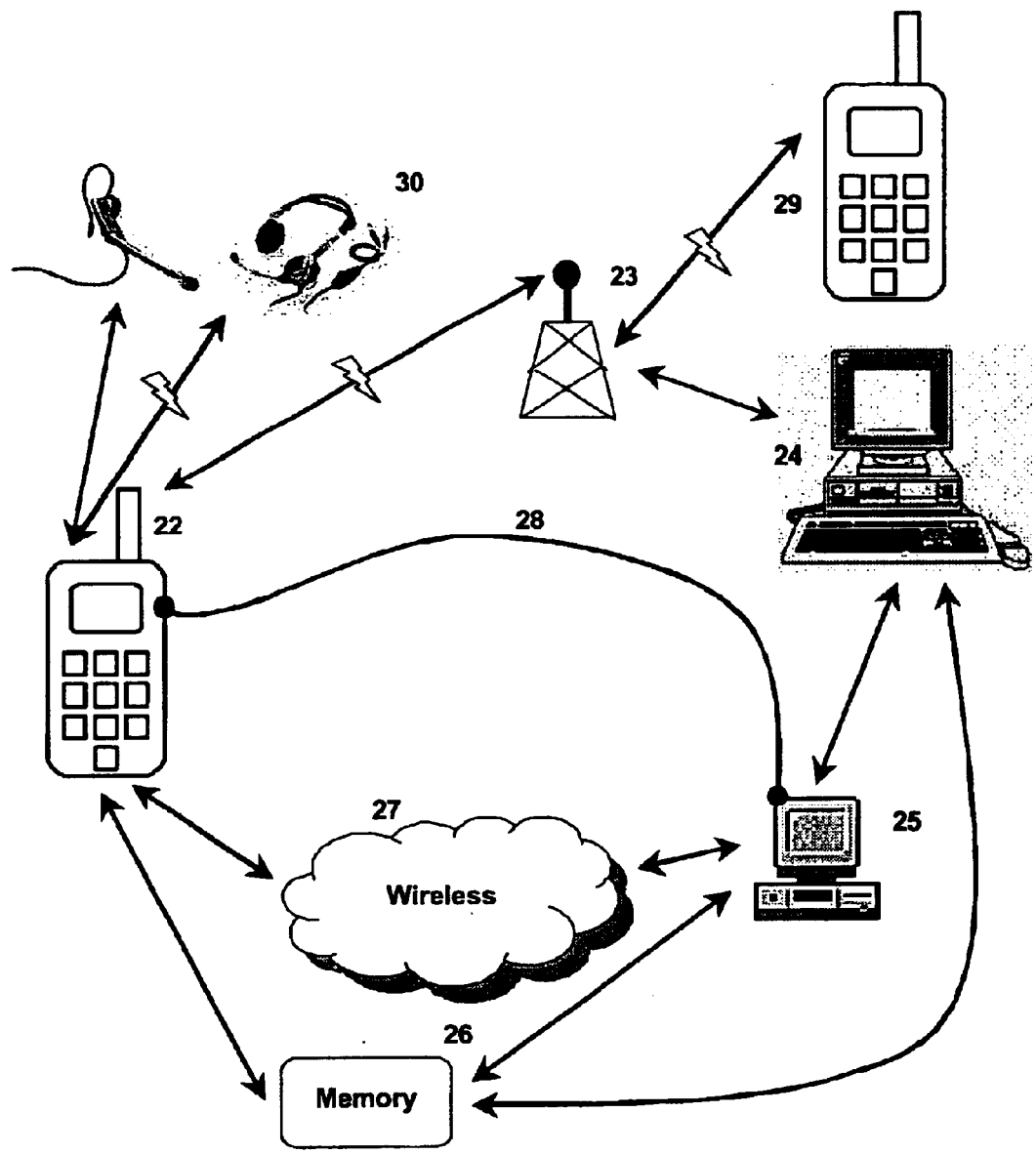
FIG. 5 illustrates a communication network, such as a telephone network, providing many ways in which audio can be transferred to and from a mobile phone, and the components where audio processing can be accomplished, according to the present invention.

The personal choice of an individual may be important in setting customization parameters for delivery of enhanced audio. Similar to the audio delivery section to follow, the creation of personal choice of audio requires generation of example audio sections to allow the user to choose preferences. FIG. 5 schematically shows audio delivery and use for a mobile phone. The audio sources described are used alone or in various combinations to present the user with audio selections upon which preference decisions may be made. Several interactive user interface methods of obtaining user preference are applied by the mobile phone, or other system, including the two alternative forced choice test protocol, the three alternative forced choice test protocol, matrix navigation test protocols, or staircase test protocols to get user feedback of preference.

Two alternative forced choice (2AFC) test protocols involve presentation of two audio choices, and forcing the user to select the one which sounds better. This choice could be followed by other 2AFC presentations, or upon satisfactory determination of preference setting the preference profile to the last selection of the user. Three alternative forced choice (3AFC) presents the user with three alternatives, two of which are the same and the third which is different. Again, navigation through the forced choices will allow, at the conclusion of the test, determination of the user's preference profile.

Matrix navigation would be presentation of audio that is customized in one or several variables, and depending on user choice, establishing that choice as a vector in personalization. Subsequent presentations of audio customization choices may explore further modification on that vector, and allowing the user to fine tune either one or more variables at each selection of preference.

Staircase test protocols involve presentation of an audio choice, then providing the means for the user to adjust the sound until the user picks a setting that sounds best to the user. The adjustment means on a mobile phone could, for example, be the volume control buttons (physical or logical) or other up/down adjustment means to allow the user to scroll through selections.

As shown in FIG. 5, audio presented over the mobile phone 22 may have many sources as the mobile phone becomes more complex. The most traditional path for mobile phone audio is audio from another land or mobile phone 29 through a transceiver system or central switching station 23 to the mobile phone 22 where customization is desired. Other potential audio types could be audio data generated at remote systems 24, whether stored audio or automated response systems. Another audio source could come from a local processing system 25 and be transferred to the mobile phone through a memory storage device 26, a local wireless link 27, or a direct wire link 28. The local processing system 25 could be a PC that is connected to network resources such as processing system 24 where audio data is obtained, then transferred to the mobile phone 22. The memory storage device 26 could be programmed at a remote resource 24 and then shipped to or transferred to the mobile phone 22 to transfer audio data.

Customized audio data could be presented to the user through the mobile phone or through accessories 30 such as headsets.

Figure 6:
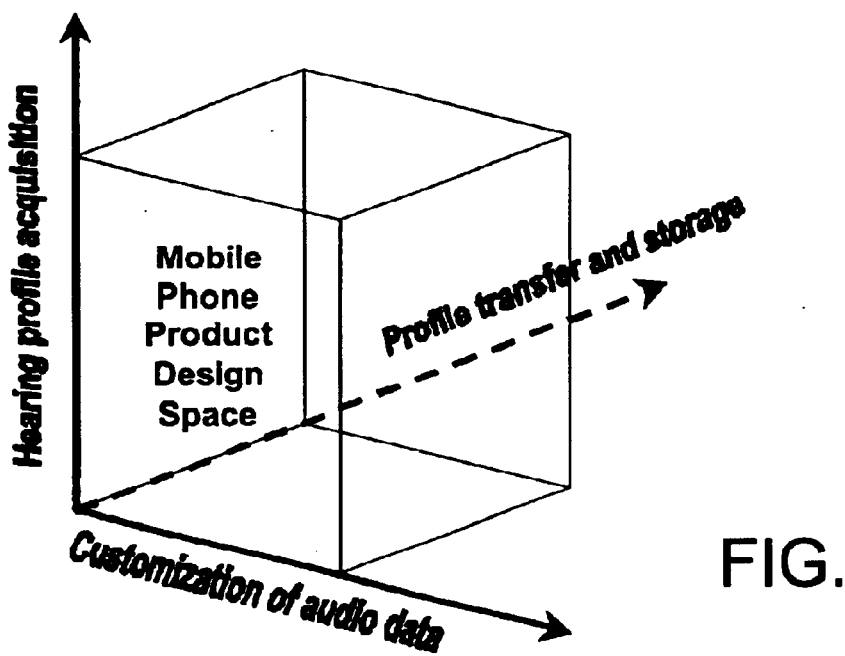
FIG. 6 shows three orthogonal design space axes defining possibilities for how the generation of customized audio data according to personal hearing profile is delivered to the end user.

FIG. 6 conceptually shows a mobile phone product (or other personal communication device) design space including the intersection of the three variables—hearing profile acquisition, profile transfer and storage, and customization of audio data—that define the possible means of personalization of audio. FIG. 3 illustrates several unique ways in which a hearing profile may be obtaining using the mobile phone system, the first variable of FIG. 6. As shown in Table 1 below, there are two distinct components of obtaining the hearing profile: (1) test algorithm or choice matrix location, and (2) sound generation location. Including separation of a test algorithm from a choice matrix, the combination of these variables leaves six methods for acquisition of a hearing profile. The other two variables in the design space for personalization are the transfer and storage of a hearing profile, and the customization of audio data.

The transfer of a hearing profile can either be automated, or depend on user interaction. In addition, the profile can be either stored locally or transferred to a remote system. These variables combine to make at least six different methods of transferring and storing the hearing profile.

Customization of audio data can be accomplished by using systems remote from the mobile phone, and delivering the customized or personalized audio to the mobile phone for playback. The alternative is to deliver unprocessed audio to the mobile phone, and use the resources of the mobile phone or an accessory to personalize the audio.

TABLE 1

| Hearing profile acquisition | A1 | Test algorithm local | Sound generation local |
|---|---|---|---|
| | A2 | Test algorithm local | Sound generation remote |
| | A3 | Test algorithm remote | Sound generation remote |
| | A4 | Test algorithm remote | Sound generation local |
| | A5 | Choice matrix | Sound generation local |
| | A6 | Choice matrix | Sound generation remote |
| Profile transfer and storage | B1 | No user interaction | Local storage |
| | B2 | User interaction | Local storage |
| | B3 | Transfer to remote | Local storage |
| | B4 | Transfer to local | Remote storage |
| | B5 | User interaction | Remote storage |
| | B6 | No user interaction | Remote storage |
| Customization of audio data | C1 | Remote customization | Delivery to local |
| | C2 | Generic audio delivery | Customization locally |

Figure 7:
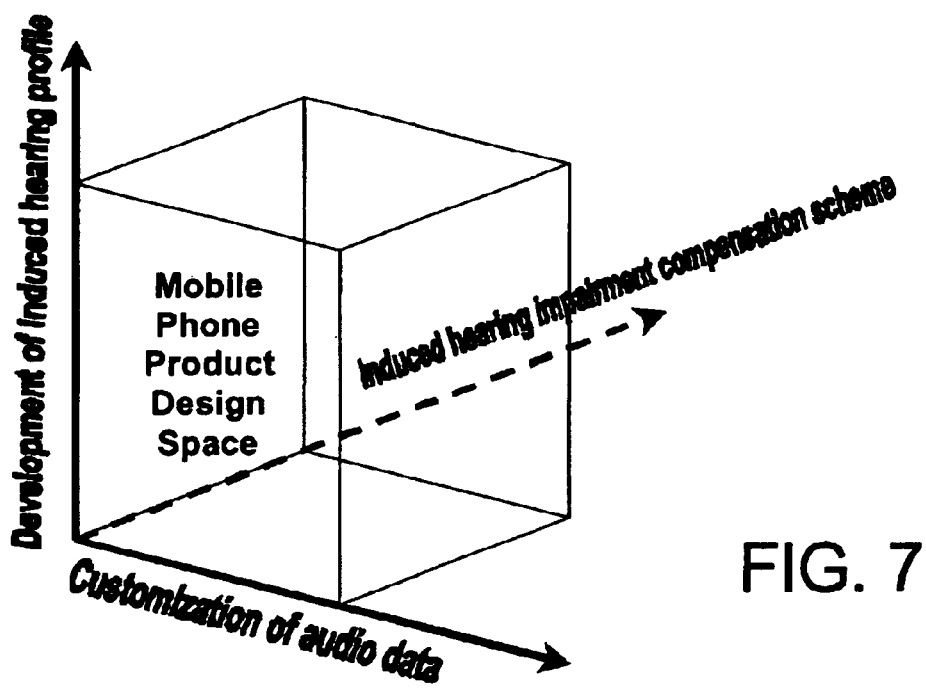
FIG. 7 shows three orthogonal design space axes defining possibilities for how the generation of customized audio data according to noise induced hearing profile is delivered to the end user.

FIG. 7 conceptually shows a mobile phone product (or other personal communication device) design space including the intersection of the three variables—development of induced hearing loss profile, induced hearing loss compensation scheme, and customization of audio data—that define the possible means of audio customization to compensate for noise induced hearing impairments.

FIG. 4 illustrates several unique ways in which a noise induced hearing profile may be obtaining using the mobile phone system, the first variable of FIG. 7. As shown in Table 2 below, there are several distinct steps in developing the induced hearing profile: direct or indirect noise sensing, and location and degree of quantification of noise. The combination addressed in Table 2, of these variables leaves six methods for developing the induced hearing profile. The other two variables in the design space for audio customization are the compensation scheme, and the customization of audio data.

The compensation scheme for induced hearing impairment can be active, passive or no monitoring of the environment. Once the environment is monitored, whether actively or passively, compensation can be dynamic or continuously changed, changed in an incremental fashion, or a single setting that is either on or off. If there is no monitoring, then the environmental compensation algorithm can be always on for products that are know to be used in noisy environments.

Customization of audio data can be accomplished by using systems remote from the mobile phone, and delivering the customized or noise compensated audio to the mobile phone for playback. The alternative is to deliver unprocessed audio to the mobile phone, and use the resources of the mobile phone or an accessory to customize the audio to compensate for environmental noise.

TABLE 2

| | | | |
|---|---|---|---|
| Development of induced hearing profile | A1 | Direct noise sensing | Local noise quantification |
| | A2 | Indirect noise sensing | Local noise quantification |
| | A3 | Direct noise sensing | Remote noise quantification |
| | A4 | Indirect noise sensing | Remote noise quantification |
| | A5 | Direct noise sensing | No quantification |
| | A6 | Indirect noise sensing | No quantification |
| Induced hearing impairment compensation scheme | B1 | Active | Dynamic (continuous) |
| | B2 | Active | Incremental |
| | B3 | Active | Single setting |
| | B4 | Passive | Continuous |
| | B5 | Passive | Incremental |
| | B6 | Passive | Single setting |
| | B7 | No monitoring | Always on |
| Customization of audio data | C1 | Remote customization | Delivery to local |
| | C2 | Generic audio delivery | Customization locally |

Figure 8:
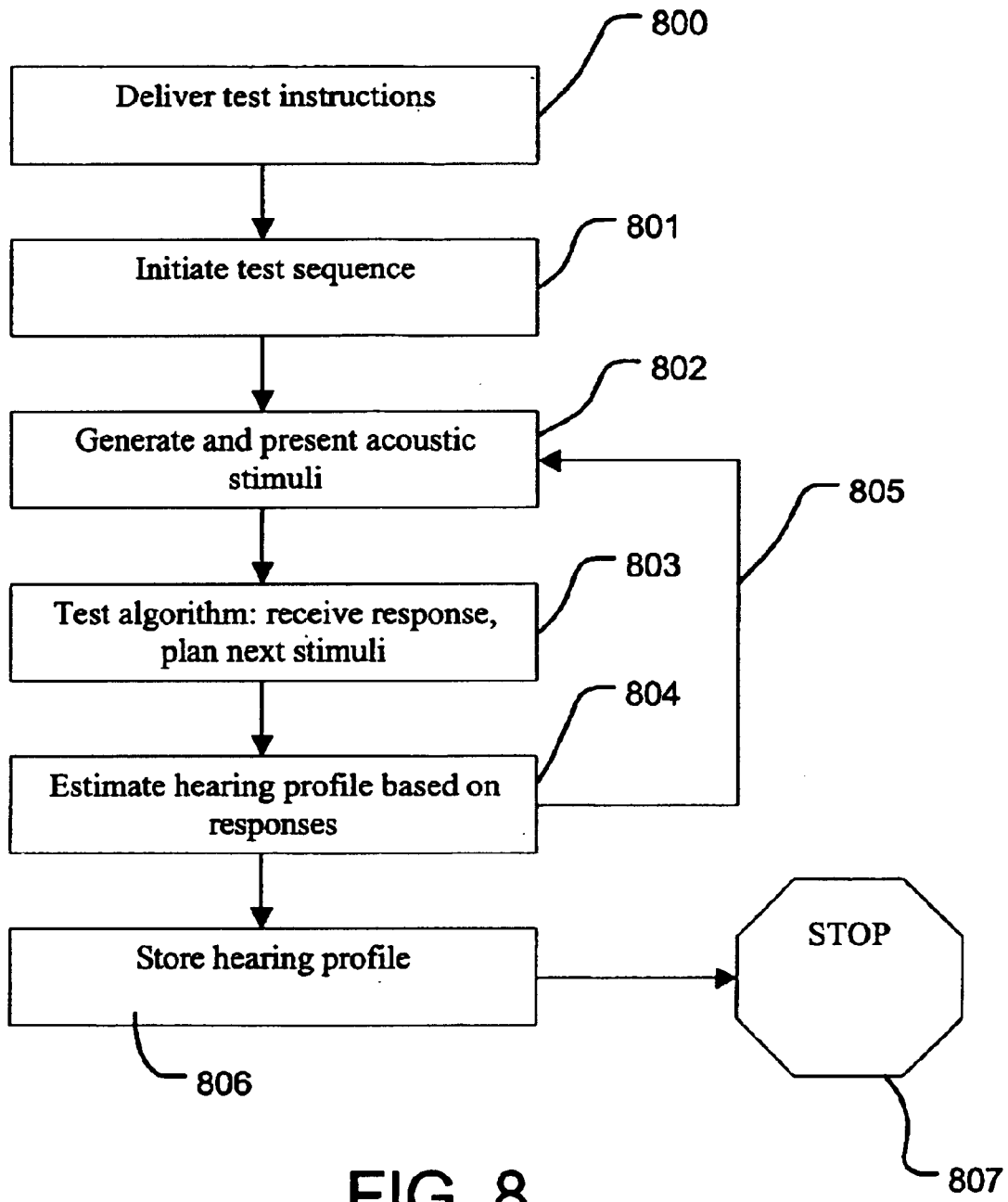
FIG. 8 is a flow chart of basic components in a process for personal hearing profile acquisition.

FIG. 8. illustrates a process for hearing profile acquisition, according to one exemplary embodiment of the present invention. The process includes delivering test instructions to the person from whom the hearing profile is to be acquired (block 800). Next, a test sequence is initiated based upon the instructions (block 801). Next, the process involves generating and presenting acoustic stimuli to the user (block 802). The algorithm next receives the user response and plans in the next stimuli for the test (block 803). The hearing profile is estimated based upon the responses (block 804). The process loops as indicated by line 805, until an end of the test is reached. The hearing profile is stored in the final step (block 806), and the algorithm stops (block 807). For each of these major steps of hearing profile acquisition, there are several example embodiments provided in outline form as follows:

Deliver test instructions (800)
  Voice based instruction
    Call a phone number to a remote system
      User dials a phone number that has been communicated to them
      User punches in a pre-programmed quick dial number
      Number automatically comes up on power up
    Sales representative communicated instructions
  Written
    Paper instruction
    Printed off of a computer
  Screen of phone
    Information transferred over mobile data link as text or graphics
    Text or graphics created by internal phone software Initiate test sequence (801)
  User push logical or physical button on phone to initiate upon prompting
  Voice recognition of a command at a remote site
  Voice recognition of a command on the mobile phone
  Starts automatically after phone is turned on for the first time Generate and present acoustic stimuli (802)
  At DSP or other acoustic processor on a mobile phone
  Generate at a remote system location and present over:
    mobile web as data transfer to mobile phone to present stimuli
    telephone transfer as circuit switched or packet switched data
  Phone to ear coupling for acoustic stimuli
    Hold phone next to ear and use built-in transducer
    Use monaural earpiece
    User binaural earpiece
  Phone to free field transducer for acoustic stimuli
    Hold phone and use internal speaker in speaker phone mode
    Hold phone and use external speaker in speaker phone mode
  Consumer interface for prompts to guide user interaction
  Prompt via voice or control signals
    From storage in phone and generated in phone
    From mobile web as data transfer to the phone to generate prompt
    From telephone call by generating voice commands
  Screen interaction
    Screen prompts from data storage in phone
    Screen prompts from mobile web data transferred to phone as needed Test algorithm: receive response, plan next stimuli (803)
  Test algorithm location for planning next stimuli
    Local on the phone from data storage on the phone
    Local on the phone transferred over mobile web link to the phone
    Remote on a local system connected to the phone (local PC, for example)
    Remote on network system resources
  Receive subject response
    User interface of phone, either physical or logical buttons
    Voice recognition at the network system resources
    Voice recognition by processor on the phone
    External device, possibly located at sales location or home
  Store subject response
    Locally in DSP or other processor or onboard data memory
    At network system resources
  Interpret response and adjust signal level
    Local in DSP or other processor
    At network system resources Estimate hearing profile based on responses (804)
  Locally in DSP or other processor
  At network system resources Store hearing profile (806)
  Profile Stored Automatically
    Local algorithm writes hearing profile into internal mobile phone data storage
    Network system resources sends data to handset that is interpreted by DSP and stored into internal mobile phone data storage
    Network system resources store profile at central location and associate profile with phone identification
  User prompted to store hearing profile
    Local processor of phone prompts with a code to user
      Via voice command
      Via presentation to screen of phone
      User inputs code and sequence to store profile
    Network system resources prompts with a code to user
      Via voice command
        Operator or technical representative sends code
        Automated generation of voice response
      Via presentation to screen of phone through data transfer to phone Once the hearing profile is acquired and stored for future use, the audio data can be customized or personalized either at the network system resource and transmitted to the phone, or delivered then personalized at a processor on the mobile phone.

Figure 9:
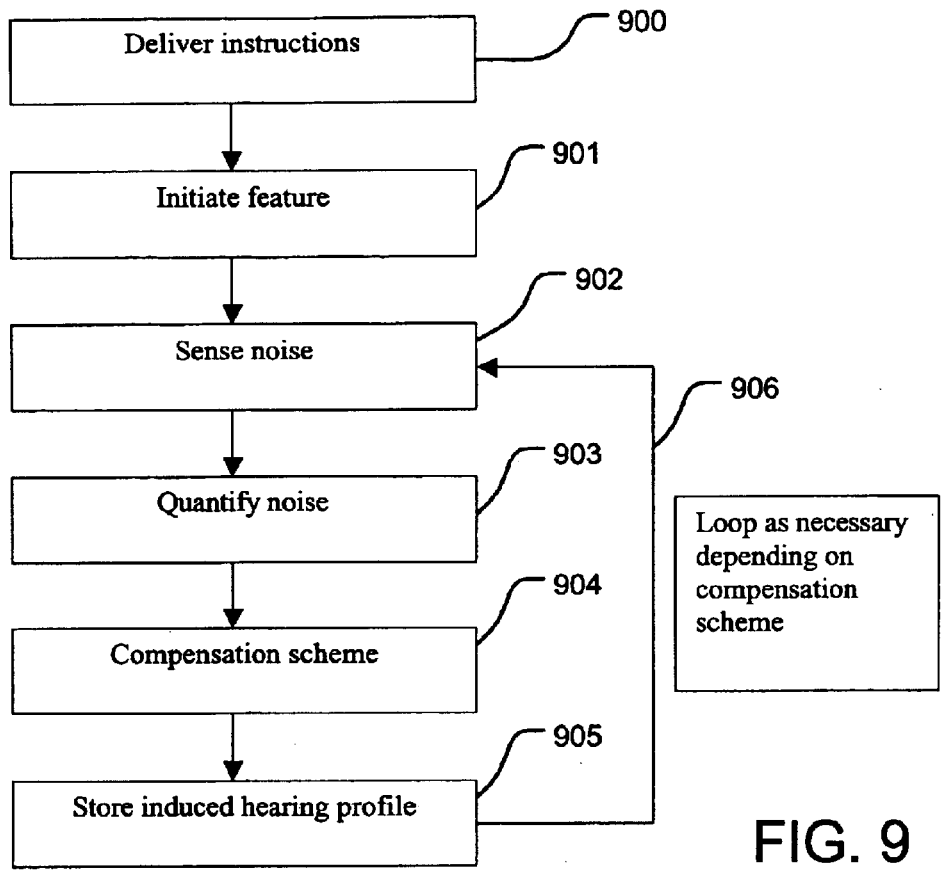
FIG. 9 is a flow chart of basic components in a process for noise induced hearing profile acquisition.

FIG. 9 illustrates a process for environmentally induced hearing profile acquisition, according to one exemplary embodiment of the present invention. The process includes delivering test instructions to the person from whom the environmentally induced hearing profile is to be acquired (block 900). Next, a feature to manage the acquisition is initiated based upon the instructions (block 901). Next, the process involves sensing or otherwise determining environmental noise (block 902). The algorithm next quantifies the noise (block 903) and determines a compensation scheme (block 904). Next, the induced profile is stored (block 905). The process loops as indicated by line 906, as necessary, depending on the compensation scheme. For each of these major steps of environmentally induced hearing profile acquisition, there are several example embodiments provided in outline form as follows:

Deliver instructions (900)
  Voice based instruction
    Call a phone number to a remote system
      User dials a phone number that has been communicated to them
      User punches in a pre-programmed quick dial number
      Number automatically comes up on power up
    Sales representative communicated instructions
  Written
    Paper instruction
    Printed off of a computer
  Screen of phone
    Information transferred over mobile data link as text or graphics
    Text or graphics created by internal phone software Initiate feature (901)
  User push logical or physical button on phone to initiate upon prompting
  User push logical or physical button on phone to initiate as needed or upon prompting
  Voice recognition of a command at a remote site
  Voice recognition of a command on the mobile phone
  Starts automatically after phone is turned on for the first time Sense noise (902)
  Direct sensing at or nearby mobile phone
    Using microphone of mobile phone
    Using microphone of an accessory such as a headset
  Indirect sensing of background noise
    Position of volume control
    Other variables that might indicate noise, like speed sensor of an automobile that predicts noise at a speed, and communicates expected noise profile to mobile phone
  No sensing Quantify noise (903)
  Locally
    Quantify using processor resources of mobile phone
    Quantify using outboard accessory attached to mobile phone
  Remotely
    Transmit noise signal to remote network resources for quantification
    Quantify and store quantization locally at remote network resource
    Quantify and return quantification (profile) to mobile phone for use
  No quantification Compensation scheme (904)
  Sensing noise signal with respect to time
    Actively sense to constantly update in time the noise profile
    Passively sense, or seldom or never update in time, in situations where noise profile is not expected to vary in time (example: airplane at cruise)
  Range of compensation settings
    As quantified noise changes continuously change compensation profile to adapt to noise
    Incrementally change compensation profile as noise crosses various thresholds of change to switch from one increment to the next
    Use few settings or a single setting based on predicted noise profile expected in the area of use of the phone Store induced hearing profile (905)
  Profile Stored Automatically
    Local algorithm writes induced hearing profile into internal mobile phone data storage
    Network system resources sends data to handset that is interpreted by DSP and stored into internal mobile phone data storage
    Network system resources store induced profile at central location and associate induced profile with phone identification
  User inputs code and sequence to select a pre-chosen induced hearing profile Once the induced hearing profile is acquired and stored for use, the audio data can be customized or personalized either at the network system resource and transmitted to the phone, or delivered then customized at a processor on the mobile phone.

A system is provided, suitable for use with wireless communication or portable entertainment devices, that compensates for the apparent hearing loss that is known to manifest itself when listening in a noisy environment. This system is of great interest especially for wireless communication devices because wireless usage patterns naturally include environments that are substantially noisier than the environments typical in traditional PSTN (Public Switched Telephone Network) usage. Such noisy environments include public social environments (restaurants, bars), in-automobile environments, public transportation environments (subways, trains, airports) and other common situations (shopping locations and city/traffic noise).

The system applies a psychoacoustic principle that listeners in noisy environments perceive signals (speech, music . . . the sounds one is trying to hear) as if they had a hearing loss. Hence, the use of techniques well known in the hearing aid industry can be applied to listening in noisy environments as a method of returning intelligibility to normal. Compression algorithms are one such well known technique. Since compression represents a distortion, indiscriminate application of compression will lead to less natural speech. As a result, it becomes important to apply the appropriate amount of compression for a given listening situation.

Figure 10:
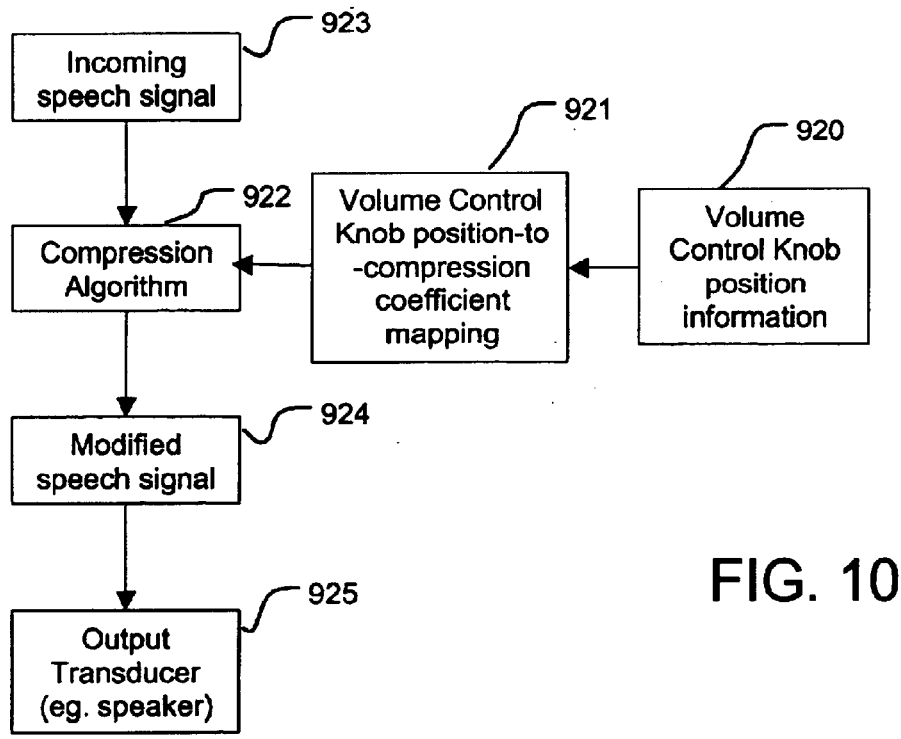
FIG. 10 is a functional drawing of the process for using volume input for controlling enhancement of sound delivery in a personal communication device.

FIG. 10 illustrates an approach for indirectly determining environment noise, by position of a volume control switch, for use in compensation for environmentally induced hearing loss profile. Thus, in a mobile phone or other personal communication device, volume control knob position information 920 is applied to volume control knob position-to-compression coefficient mapping module 921. The coefficient mapping is supplied to a compression algorithm 922. An incoming speech signal 923 is applied to the compression algorithm 922. A modified speech signal 924 results which is applied to an output transducer 925, such a speaker. Of course "volume control knob position information" refers to any information which indicates the level of a volume input switch, such as a knob, a slider, or an up/down switch pair, which is adjusted by a user of the personal communication device to set a volume level for audio output of the device.

The process includes:

Using the volume control knob position as the control signal that defines the amount of compression to apply to the incoming speech signal. The position of the control knob acts as a proxy for the environmental noise;

completing the compression processing within the wireless communications handset or portable entertainment device, and not at a central location; and specifying volume control knob position to compression mapping functions.

A number of possibilities of the mapping between volume control knob and coefficient mapping, include the following:

Compression kicks in once the volume control knob gets to a sufficiently high level that indicates that presence of background noise.

Compression increases smoothly as a function of volume control knob position.

Shape of compression is set to provide maximum relief from masking utilizing an assumed spectral shape for the noise.

Compression is uniform across frequency.

Compression starts off shaped to provide maximum relief from masking utilizing an assumed spectral shape for the noise but transitions to uniform compression as the volume knob position indicates louder background environments.

Compression shape is set to maximize the intelligibility of a portion of the signal frequency band without attempting to alleviate the apparent hearing loss in the other portion of the band. This approach may deliver sufficient intelligibility increases as low power requirements.

Compression is shaped to minimize power requirements while increasing intelligibility.

At some point along the travel of the volume control knob, further requests for more volume do not generate louder peaks but simply increase the compression rate.

A number of differentiators of this aspect of the present invention include:

The use of the volume control knob position as a proxy for environmental noise level. The major advantage to using Volume Control knob position to control the amount of compression is relative computational simplicity: With a microphone system for sensing environmental noise, the microphone signal needs to be analyzed to remove the signal due to the listener speaking in order to get a true measure of the background noise.

Processing inside the handset. Several advantages come from processing inside the handset:

Processing capability does not depend on infrastructure capabilities. Hence introduction of capability is at a substantially lower cost risk and running changes are made to the lower cost handsets.

Processing can make use of existing hardware in the handset

Processing capabilities require no additional bandwidth

Cost of the capability is easily assigned to the beneficiary

Introduction of capability is at a substantially lower cost risk and running changes are made to the lower cost handsets.

Up-grades/changes of processing hardware are relatively easy.

Coincidentally, it is recognized that compression solves problems of other difficult listening situations also. In some situations, the speaker may generate a speech signal that has larger than normal dynamic range. In such situation, the listener would want to adjust the volume such that the quietest sounds have a large effective gain while the loud sounds have less gain. This difference in desired gain levels as a function of signal level can be provided through the use of compression. The following situations are likely to lead to large dynamic range speech signals: communication to a speaker phone system, communication with individuals who are actively engaged during communication (i.e. they are on a wireless communication device and doing something), background noise in the speakers environment is changing significantly during the communication.

Similar to a mobile phone handset, portable entertainment systems are often used in high noise environments, for example exercising, outdoor urban activities, etc. Compression of high dynamic range audio entertainment signals, whether received by the audio system or generated from representative digital or analog storage representative of audio, by systems within the portable entertainment system would provide compensation for the noise induced hearing changes experienced by the listener.

Mapping of coefficients could take into account base coefficient values that are representative of a hearing impaired individual's requirements for hearing in quiet. Additional compression, whether in frequency ranges where an individual has impairment, or in frequency bands where no impairment compensation in quiet is required, would be beneficial for the additional hearing changes induced by background noise.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the appended claims.

What is claimed is:

1. A personal communication device comprising:

a transmitter/receiver coupled to a communication medium for transmitting and receiving audio signals;

control circuitry coupled to the transmitter/receiver that controls transmission, reception and processing of call and audio signals;

an audio transducer coupled to the control circuitry that renders call and audio signals audible;

a microphone coupled to the control circuitry that transduces sounds to audio signals; and said control circuitry including logic applying multiband compression to the audio signals, including generation of parameters for the multiband compression based on stored user data and based on environmental data determined while rendering the audio signals audible.

2. The device of claim 1, wherein said control circuitry includes instruction memory and an instruction execution processor.

3. The device of claim 1, wherein said control circuitry includes a digital signal processor.

4. The device of claim 1, including an input device adapted to indicate a volume level for said audio transducer, and wherein said environmental data comprises the volume level.

5. The device of claim 1, wherein said control circuitry generates said parameters of the multiband compression based on said stored user data and on said environmental data independently and in parallel in processing the audio signals.

6. The device of claim 1, wherein said control circuitry generates said parameters of the multiband compression based on said stored user data and on said environmental data independently and in series in processing the audio signals.

7. The device of claim 1, including a sensor which detects environmental noise, for providing said environmental data.

8. The device of claim 1, including logic to process environmental noise picked up by the microphone, for providing said environmental data.

9. The device of claim 1, including resources to obtain a hearing profile for a user from a remote source.

10. The device of claim 1, including resources to prompt a user to provide information specifying a hearing profile of the user.

11. The device of claim 1, including resources to prompt a user to provide information specifying a hearing profile of the user and a user preference.

12. The device of claim 1, including resources to prompt a user to provide information specifying a user preference.

13. The device of claim 1, including resources to prompt a user to provide information for use in defining a hearing profile of the user.

14. The device of claim 13, including a display, and wherein said resources include logic prompting with at least one of said audio transducer and said display, the user through a hearing test based upon user reaction to sounds, and in which said sounds are produced using said audio transducer.

15. The device of claim 1, wherein the stored user data comprises one or more of a hearing profile of a user and a user preference related to hearing, and the environmental data comprises environmental noise factors.

16. A mobile phone, comprising:
an antenna;
a transmitter/receiver coupled to the antenna for transmitting and receiving call and audio signals;
control circuitry, including a processor which executes instructions, coupled to the transmitter/receiver which controls the transmission and reception of the call and audio signals;
an audio transducer coupled to the control circuitry;
a microphone coupled to the control circuitry;
a memory coupled to the control circuitry holding instructions, executable by the processor, to apply multiband compression to the audio signals, including generation of parameters for the multiband compression based on stored user data and based on environmental data determined while rendering the audio signals audible.

17. The mobile phone of claim 16, including an input device adapted to indicate a volume level for said audio transducer, and wherein said environmental data comprises the volume level.

18. The mobile phone of claim 16, wherein said control circuitry generates said parameters of the multiband compression based on said stored user data and on said environmental data independently and in parallel in processing the audio signals.

19. The mobile phone of claim 16, wherein said control generates said parameters of the multiband compression based on said stored user data and on said environmental data independently and in series in processing the audio signals.

20. The mobile phone of claim 16, including a sensor which detects environmental noise, for providing said environmental data.

21. The mobile phone of claim 16, including logic to process environmental noise picked up by the microphone, for providing said environmental data.

22. The mobile phone of claim 16, wherein the memory holds instructions to obtain a hearing profile for a user from a remote source.

23. The mobile phone of claim 16, wherein the memory holds instructions to prompt a user to provide information specifying a hearing profile of the user.

24. The mobile phone of claim 16, wherein the memory holds instructions to prompt a user to provide information specifying a hearing profile of the user and a user preference.

25. The mobile phone of claim 16, wherein the memory holds instructions to prompt a user to provide information specifying a user preference.

26. The mobile phone of claim 16, wherein the memory holds instructions to prompt a user to provide information for use in defining a hearing profile of the user.

27. The mobile phone of claim 26, including a display, and wherein the memory holds instructions to prompt with at least one of said audio transducer and said display, the user through a hearing test based upon user reaction to sounds, and in which said sounds are produced using said audio transducer.

28. The mobile phone of claim 16, wherein the stored user data comprises one or more of a hearing profile of a user and a user preference related to hearing, and the environmental data comprises environmental noise factors.

29. A telephone communication system comprising:
a service provider; and
a mobile phone comprising
an antenna for transmitting and receiving call and voice signals;
a transmitter/receiver coupled to the antenna for transmitting and receiving the call and voice signals;
control circuitry, including a processor which executes instructions, coupled to the transmitter/receiver for controlling the transmission and reception of the call and audio signals;
an audio transducer coupled to the control circuitry for amplifying the call and audio signals;
a microphone coupled to the control circuitry for receiving audio signals;
a memory coupled to the control circuitry holding instructions, executable by the processor, for applying multiband compression to the audio signals, including generation of parameters for the multiband compression based on stored user data and based on environmental data determined while rendering the audio signals audible, and for communicating with the service provider.

30. The telephone communication system of claim 29, wherein the mobile phone includes an input device adapted to indicate a volume level for said audio transducer, and wherein said environmental data comprises the volume level.

31. The telephone communication system of claim 29, wherein the control circuitry generates said parameters of the multiband compression based on said stored user data and on said environmental data independently and in parallel in processing the audio signals.

32. The telephone communication system of claim 29, wherein the control circuitry generates said parameters of the multiband compression based on said stored user data and on said environmental data independently and in series in processing the audio signals.

33. The telephone communication system of claim 29, wherein the mobile phone includes a sensor which detects environmental noise, for providing said environmental data.

34. The telephone communication system of claim 29, wherein the mobile phone includes logic to process environmental noise picked up by the microphone, for providing said environmental data.

35. The telephone communication system of claim 29, wherein the memory holds instructions to obtain a hearing profile for a user from a remote source.

36. The telephone communication system of claim 29, wherein the memory holds instructions to prompt a user to provide information specifying a hearing profile of the user.

37. The telephone communication system of claim 29, wherein the memory holds instructions to prompt a user to provide information specifying a bearing profile of the user and a user preference.

38. The telephone communication system of claim 29, wherein the memory holds instructions to prompt a user to provide information specifying a user preference.

39. The telephone communication system of claim 29, wherein the memory holds instructions to prompt a user to provide information for use in defining a hearing profile of the user.

40. The telephone communication system of claim 29, wherein the mobile phone includes a display, and wherein the memory holds instructions to prompt with at least one of said audio transducer and said display, the user through a hearing test based upon user reaction to sounds, and in which said sounds are produced using said audio transducer.

41. The telephone communication system of claim 29, wherein the stored user data comprises one or more of a hearing profile of a user and a user preference related to hearing, and the environmental data comprises environmental noise factors.

* * * * *